United States Patent
Okroj et al.

(10) Patent No.: US 11,414,468 B2
(45) Date of Patent: Aug. 16, 2022

(54) FACTOR B AND C2 PROTEIN POINT MUTANTS, A METHOD FOR ENHANCING THE ACTIVITY OF ANTI-CANCER ANTIBODIES, THE PHARMACEUTICAL COMPOSITION AND THE USE OF MUTANTS

(71) Applicant: GDANSKI UNIWERSYTET MEDYCZNY, Gdansk (PL)

(72) Inventors: Marcin Okroj, Gdansk (PL); Anna Felberg-Mietka, Gdansk (PL); Aleksandra Urban, Gdansk (PL)

(73) Assignee: GDANSKI UNIWERSYTET MEDYCZNY, Gdańsk (PL)

( * ) Notice: Subject to any disclaimer, the term of this patent is extended or adjusted under 35 U.S.C. 154(b) by 0 days.

(21) Appl. No.: 17/045,058

(22) PCT Filed: Apr. 3, 2019

(86) PCT No.: PCT/PL2019/000024
§ 371 (c)(1),
(2) Date: Oct. 2, 2020

(87) PCT Pub. No.: WO2019/194689
PCT Pub. Date: Oct. 10, 2019

(65) Prior Publication Data
US 2021/0163553 A1 Jun. 3, 2021

(30) Foreign Application Priority Data
Apr. 4, 2018 (PL) .......................... 425133

(51) Int. Cl.
*C07K 14/47* (2006.01)
*A61K 38/00* (2006.01)

(52) U.S. Cl.
CPC ............ *C07K 14/472* (2013.01); *A61K 38/00* (2013.01)

(58) Field of Classification Search
CPC .......... A61K 39/39558; A61K 2300/00; A61K 38/00; A61P 35/02; C07K 14/472;
(Continued)

(56) References Cited

U.S. PATENT DOCUMENTS

| | | |
|---|---|---|
| 2008/0003646 A1 | 1/2008 | Begent et al. |
| 2011/0059072 A1 | 3/2011 | Beliard et al. |
| 2019/0016766 A1 | 1/2019 | Benjamin et al. |

FOREIGN PATENT DOCUMENTS

WO    2012151468 A1    11/2012

OTHER PUBLICATIONS

NM_001710, [*Homo sapiens* complement factor B (CFB), mRNA], NM_001710.4, (May 11, 2008), 4 pages, also available at https://www.ncbi.nlm.nih.gov/nuccore/NM_001710 (last visited May 24, 2021) (Year: 2008).*

(Continued)

*Primary Examiner* — Randall L Beane
(74) *Attorney, Agent, or Firm* — Katten Muchin Rosenman LLP

(57) ABSTRACT

The subject of this invention is point mutants of human proteins constituting the complement system's C3 and C5 convertases, where the mutation are as follows: For the factor B: —D279G, F286L, K323E, Y363A; D279G_F286L_K323E_Y363A—quadruple mutant; For the C2 protein: —C261A, Q.263G, Y347A, L348A; T442Q, double mutants C261A_Q263G and Y347A_Q263G, triple mutant Y347A_Q263G_T442Q The subject of this invention is the method of enhancing the activity of the anti-cancer antibodies, which includes the addition of mutants defined above. The subject of this invention is the pharma- (Continued)

ceutical composition, which includes the therapeutically effective number of mutants defined above. The subject of this invention is the use of mutants defined above to enhance the cytotoxic activity of anti-cancer antibodies in therapy and in the treatment of neoplastic diseases.

12 Claims, 4 Drawing Sheets

Specification includes a Sequence Listing.

(58) Field of Classification Search
CPC ............ C07K 16/2887; C07K 2317/73; C07K 2317/734; C12N 9/647; C12Y 304/21085
See application file for complete search history.

(56) References Cited

OTHER PUBLICATIONS

NM_000063.5, [*Homo sapiens* complement C2 (C2), transcript variant 1, mRNA], NM_000063.5 (Sep. 7, 2013), 5 pages, also available at https://www.ncbi.nlm.nih.gov/nuccore/NM_000063.5 (last visited May 24, 2021) (Year: 2013).*

2ODP_A, [Chain A, Complement C2], PDB: 2ODP_A, 3 pages, attached as a pdf (Dec. 7, 2012), also available at https://www.ncbi.nlm.nih.gov/protein/2ODP_A (last visited May 24, 2021) (Year: 2012).*

Livingstone et al., Protein sequence alignments: a strategy for the hierarchical analysis of residue conservation, CABIOS, vol. 9(6): 745-756 (1993) (Year: 1993).*

International Search Report and Written Opinion dated Aug. 5, 2019, from the corresponding PCT/PL2019/000024 15 sheets.

Database ENA [Online] EBI; Jun. 2, 2015 (Jun. 2, 2015), Sahni N. et al.: "AKI70377; SV 1; linear; other DNA; STD; SYN; 2292 BP—synthetic construct partial CFB", XP002793141, Database accession No. AKI70377, the whole document.

Database ENA [Online] EBI; Jun. 2, 2015 (Jun. 2, 2015), Sahni N. et al.: "AKI70378; SV 1; linear; other DNA; STD; SYN; 2292 BP—synthetic construct partial CFB", XP002793142, Database accession No. AKI70378, the whole document.

Database UniParc [Online] Uniprot; Jan. 15, 2015 (Jan. 15, 2015), UniParc—UPI0000F0A514: "UniParc—UPI0000F0A514", XP002793143, Database accession No. UPI0000F0A514.

De Jorge Elena Goicoechea et al: "Gain-of-function mutations in complement factor B are assocated with atypical hemolytic uremic syndrome", Proceedings of the National Academy of Sciences of the United States of America, vol. 104, No. 1, Jan. 2007 (Jan. 2007), pp. 240-245, XP055162429, ISSN: 0027-8424, the whole document.

Harris Claire L et al: "The aHUS-associated BF mutations F286L and K323E stabilise the alternative pathway C3 convertase", Molecular Immunology, vol. 44, No. 1-3, Sp. Iss. SI, Jan. 2007 (Jan. 2007), p. 181, XP027451964, & 21st International Complement Workshop; Beijing, Peoples R China; Oct. 20-27, 2006, ISSN: 0161-5890, the whole document.

S.-Y. Wang et al: "Depletion of the C3 component of complement enhances the ability of rituximab-coated target cells to activate human NK cells and improves the efficacy of monoclonal antibody therapy in an in vivo model", Blood, vol. 114, No. 26, Dec. 17, 2009 (Dec. 17, 2009), pp. 5322-5330, XP055046784, ISSN: 0006-4971, DOI:10.1182/blood-2009-01-200469 p. 5325, right-hand column p. 5326, column both figure 7.

Afshar-Kharghan Vahid: "The role of the complement system in cancer.", The Journal of Clinical Investigation Mar. 1, 2017, vol. 127, No. 3, Mar. 1, 2017 (Mar. 1, 2017), pp. 780-789, XP002793144, ISSN: 1558-8238, the whole document, abstract.

Stasilojc G, Osterborg A, Blom AM, Okroj M. New perspectives on complement mediated immunotherapy. Cancer Treat Rev 2016; 45:68-75.

Fishelson Z, Donin N, Zell S, Schultz S, Kirschfink M. Obstacles to cancer immunotherapy: expression of membrane complement regulatory proteins (mCRPs) in tumors.Mol Immunol 2003; 40:109-23.

Mamidi S, Hone S, Teufel C, Sellner L, Zenz T, Kirschfink M. Neutralization of membrane complement regulators improves complement-dependent effector functions of therapeutic anticancer antibodies targeting leukemic cells. OncoImmunology 4:3, e979688; Mar. 2015, e979688-1 to e979688-12.

Macor P, Secco E, Mezzaroba N, Zorzet S, Durigutto P, Gaiotto T, et al. Bispecific antibodies targeting tumor-associated antigens and neutralizing complement regulators increase the efficacy of antibody-based immunotherapy in mice. Leukemia 2015; 29:406-14.

Okroj M, Eriksson I, Osterborg A, Blom AM. Killing of CLL and NHL cells by rituximab and ofatumumab under limited availability of complement. Med Oncol 2013; 30:759, pp. 1-8.

* cited by examiner

Seq.1

```
  1  mgsnlspqlc lmpfilglls ggvtttpwsl arpqgscsle gveikggsfr llqegqaley
 61  vcpsgfypyp vqtrtcrstg swstlktqdq ktvrkaecra ihcprphdfe ngeywprspy
121  ynvsdeisfh cydgytlrgs anrtcqvngr wsgqtaicdn gagycsnpgi pigtrkvgsq
181  yrledsvtyh csrgltlrgs qrrtcqeggs wsgtepscqd sfmydtpqev aeaflsslte
241  tiegvdaedg hgpgeqqkrk ivldpsgsmn iylvldgsds igasnftgak kclvnliekv
301  asygvkpryg lvtyatypki wvkvseadss nadwvtkqln einyedhklk sgtntkkalq
361  avysmmswpd dvppegwnrt rhviilmtdg lhnmggdpit videirdlly igkdrknpre
421  dyldvyvfgv gplvnqvnin alaskkdneq hvfkvkdmen ledvfyqmid esqslslcgm
481  vwehrkgtdy hkqpwqakis virpskghes cmgavvseyf vltaahcftv ddkehsikvs
541  vggekrdlei evvlfhpnyn ingkkeagip efydydvali klknklkygq tirpiclpct
601  egttralrlp ptttcqqqke ellpaqdika lfvseeekkl trkevyikng dkkgscerda
661  qyapgydkvk disevvtprf lctggvspya dpntcrgdsg gplivhkrsr fiqvgviswg
721  vvdvcknqkr qkqvpahard fhinlfqvlp wlkeklqded lgfl
```

FIG. 7

Seq.2

```
  1  mgplmvlfcl lflypglads apscpqnvni sggtftlshg wapgslltys cpqglypspa
 61  srlckssgqw qtpgatrsls kavckpvrcp apvsfengiy tprlgsypvg gnvsfecedg
121  filrgspvrq crpngmwdge tavcdngagh cpnpgislga vrtgfrfghg dkvryrcssn
181  lvltgssere cqgngvwsgt epicrqpysy dfpedvapal gtsfshmlga tnptqktkes
241  lgrkiqiqrs ghlnlyllld csqsvsendf lifkesaslm vdrifsfein vsvaiitfas
301  epkvlmsvln dnsrdmtevi sslenanykd hengtgtnty aalnsvylmm nnqmrllgme
361  tmawqeirha iilltdgksn mggspktavd hireilninq krndyldiya igvgkldvdw
421  relnelgskk dgerhafilq dtkalhqvfe hmldvskltd ticgvgnmsa nasdqertpw
481  hvtikpksqe tcrgalisdq wvltaahcfr dgndhslwrv nvgdpksqwg kefliekavi
541  spgfdvfakk nqgilefygd diallklaqk vkmstharpi clpctmeanl alrrpqgstc
601  rdhenellnk qsvpahfval ngsklninlk mgvewtscae vvsqektmfp nltdvrevvt
661  dqflcsgtqe despckgesg gavflerrfr ffqvglvswg lynpclgsad knsrkraprs
721  kvppprdfhi nlfrmqpwlr qhlgdvlnfl pl
```

FIG. 8

SEQUENCE LISTING

```
<160> NUMBER OF SEQ ID NOS: 2

<210> SEQ ID NO 1
<211> LENGTH: 764
<212> TYPE: PRT
<213> ORGANISM: Homo sapiens

<400> SEQUENCE: 1

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
```

```
            180                 185                 190
Arg Gly Leu Thr Leu Arg Gly Ser Gln Arg Thr Cys Gln Glu Gly
        195                 200                 205

Gly Ser Trp Ser Gly Thr Glu Pro Ser Cys Gln Asp Ser Phe Met Tyr
        210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
        260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
        290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
        340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
        370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
        420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
        450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
        500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
        530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
        580                 585                 590

Arg Pro Ile Cys Leu Pro Cys Thr Glu Gly Thr Thr Arg Ala Leu Arg
        595                 600                 605
```

```
Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
                660                 665                 670

Ser Glu Val Val Thr Pro Arg Phe Leu Cys Thr Gly Gly Val Ser Pro
                675                 680                 685

Tyr Ala Asp Pro Asn Thr Cys Arg Gly Asp Ser Gly Gly Pro Leu Ile
                690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
                740                 745                 750

Lys Glu Lys Leu Gln Asp Glu Asp Leu Gly Phe Leu
                755                 760

<210> SEQ ID NO 2
<211> LENGTH: 752
<212> TYPE: PRT
<213> ORGANISM: Homo sapiens

<400> SEQUENCE: 2

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
                20                  25                  30

Gly Thr Phe Thr Leu Ser His Gly Trp Ala Pro Gly Ser Leu Leu Thr
            35                  40                  45

Tyr Ser Cys Pro Gln Gly Leu Tyr Pro Ser Pro Ala Ser Arg Leu Cys
50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
                100                 105                 110

Val Ser Phe Glu Cys Glu Asp Gly Phe Ile Leu Arg Gly Ser Pro Val
            115                 120                 125

Arg Gln Cys Arg Pro Asn Gly Met Trp Asp Gly Glu Thr Ala Val Cys
        130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
                180                 185                 190

Gly Asn Gly Val Trp Ser Gly Thr Glu Pro Ile Cys Arg Gln Pro Tyr
            195                 200                 205

Ser Tyr Asp Phe Pro Glu Asp Val Ala Pro Ala Leu Gly Thr Ser Phe
```

```
            210                 215                 220
Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
                260                 265                 270

Phe Lys Glu Ser Ala Ser Leu Met Val Asp Arg Ile Phe Ser Phe Glu
            275                 280                 285

Ile Asn Val Ser Val Ala Ile Ile Thr Phe Ala Ser Glu Pro Lys Val
            290                 295                 300

Leu Met Ser Val Leu Asn Asp Asn Ser Arg Asp Met Thr Glu Val Ile
305                 310                 315                 320

Ser Ser Leu Glu Asn Ala Asn Tyr Lys Asp His Glu Asn Gly Thr Gly
                325                 330                 335

Thr Asn Thr Tyr Ala Ala Leu Asn Ser Val Tyr Leu Met Met Asn Asn
                340                 345                 350

Gln Met Arg Leu Leu Gly Met Glu Thr Met Ala Trp Gln Glu Ile Arg
            355                 360                 365

His Ala Ile Ile Leu Leu Thr Asp Gly Lys Ser Asn Met Gly Gly Ser
370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
                405                 410                 415

Asp Val Asp Trp Arg Glu Leu Asn Glu Leu Gly Ser Lys Lys Asp Gly
                420                 425                 430

Glu Arg His Ala Phe Ile Leu Gln Asp Thr Lys Ala Leu His Gln Val
            435                 440                 445

Phe Glu His Met Leu Asp Val Ser Lys Leu Thr Asp Thr Ile Cys Gly
450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
                500                 505                 510

Asn Asp His Ser Leu Trp Arg Val Asn Val Gly Asp Pro Lys Ser Gln
            515                 520                 525

Trp Gly Lys Glu Phe Leu Ile Glu Lys Ala Val Ile Ser Pro Gly Phe
530                 535                 540

Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
                565                 570                 575

Ala Arg Pro Ile Cys Leu Pro Cys Thr Met Glu Ala Asn Leu Ala Leu
            580                 585                 590

Arg Arg Pro Gln Gly Ser Thr Cys Arg Asp His Glu Asn Glu Leu Leu
            595                 600                 605

Asn Lys Gln Ser Val Pro Ala His Phe Val Ala Leu Asn Gly Ser Lys
            610                 615                 620

Leu Asn Ile Asn Leu Lys Met Gly Val Glu Trp Thr Ser Cys Ala Glu
625                 630                 635                 640
```

```
Val Val Ser Gln Glu Lys Thr Met Phe Pro Asn Leu Thr Asp Val Arg
            645             650             655

Glu Val Val Thr Asp Gln Phe Leu Cys Ser Gly Thr Gln Glu Asp Glu
        660             665             670

Ser Pro Cys Lys Gly Glu Ser Gly Gly Ala Val Phe Leu Glu Arg Arg
        675             680             685

Phe Arg Phe Phe Gln Val Gly Leu Val Ser Trp Gly Leu Tyr Asn Pro
        690             695             700

Cys Leu Gly Ser Ala Asp Lys Asn Ser Arg Lys Arg Ala Pro Arg Ser
705             710             715             720

Lys Val Pro Pro Pro Arg Asp Phe His Ile Asn Leu Phe Arg Met Gln
            725             730             735

Pro Trp Leu Arg Gln His Leu Gly Asp Val Leu Asn Phe Leu Pro Leu
            740             745             750
```

FACTOR B AND C2 PROTEIN POINT MUTANTS, A METHOD FOR ENHANCING THE ACTIVITY OF ANTI-CANCER ANTIBODIES, THE PHARMACEUTICAL COMPOSITION AND THE USE OF MUTANTS

INCORPORATION-BY-REFERENCE OF SEQUENCE LISTING

The material in the accompanying sequence listing is hereby incorporated by reference in its entirety into this application. The accompanying file, named Sequence Listing 385991-00009_ST25, was created on Jul. 12, 2021, and is 13.1 KB.

The subject of the invention is directed to mutants of human proteins which are part of the complement system's C3 and C5 convertases, specifically factor B and the C2 protein. In addition, methods to enhance the effectiveness of anticancer antibodies by adding the mutant proteins of factor B or the C2 protein to such antibodies is also disclosed. The subject of the invention is also directed to a pharmaceutical composition that includes a therapeutically effective amount of the disclosed mutant proteins and their use in enhancing the cytotoxic activity of anticancer antibodies in therapy and in the treatment on neoplastic diseases.

The introduction of cancer cell determinants recognizing antibodies to a standard cancer therapy has contributed to a significant prolonging of the patient survival time and to a reduction in the tumor progression rate. The rituximab recognizing the CD20 molecule, used in leukemia and lymphoma treatment, is a prototype of the therapeutic anticancer antibody.

Rituximab, and a set of other antibodies approved for clinical use, kills cancer cells in cooperation with the human immune system. The binding of the antibody to the surface of a cancer cell activates the complement system—an enzymatic cascade located in the blood serum, whose elements, as a result of the activation, is inserted into the cell membrane of the target cell. The final effect of the complement system activation is a formation of pores and an osmotic lysis of the target cell. Additionally, the complement components' coating of the cancer cell facilitates its absorption by other cells of the immune system by means of phagocytosis.

Although the anticancer antibodies have revolutionized the treatment, clinical response does not concern all of the patients; moreover, a resistance to the therapy occurs in some cases. One of the reasons for resistance to the therapeutics operating through the complement system is the overexpression of complement system inhibitors on the cancer cell surface and a depletion of the complement proteins pool through the system activation by the antibodies, which results in insufficient complement activity during subsequent drug administrations.

The description of the US2011059072 A invention discloses the method of obtaining and selecting monoclonal antibodies by means of the ADCC type test, which are capable of activating the type III Fcγ receptors and have a particular glycan structure.

The description of the US2008003646 A invention discloses improved antibodies against tumor surface antigens and their use in cancer treatment. Particularly interesting are the highly stable, humanized antibodies with a high affinity to the carcinoembryonic antigen (CEA), specifically the sm3E antibody that is derived from the scFv MFE-23 antibody. Such antibody modifications can potentially improve the therapeutic efficacy.

The invention being the subject of this application suggests a solution in the form of anticancer antibodies supplementation with mutant human proteins which are part of the enzymatic complexes (convertases) responsible for the C3 and C5 complement protein proteolysis to their C3b and C5b active fragments. Factor B, which is involved in the building of convertases, is a component of the alternative pathway of the complement system, as well as the C2 protein, which plays an analogous role in the classical pathway of the complement system, are examples of such proteins. Suitable mutations of the abovementioned proteins are the ones that affect convertases interaction with their inhibitors, by which both activity and the half-life of the enzyme complex alike is greatly extended, and the production of the C3b and C5b fragments optimal for the cytotoxic effect is ensured.

The C2 and factor B mutants added in the in vitro test on CD20-positive lymphoma cells to the human serum and a specific anti-CD20 antibody caused a complete lysis of the cells moderately sensitive to anti-CD20 antibodies. Additionally, the C2 protein mutants caused a statistically significant increase in the death rate of the cells weakly sensitive to anti-CD20 antibodies. Importantly, the increase in the cytotoxic effect, both in the moderately and weakly sensitive to anti-CD20 antibodies lines, was not possible to obtain through increasing the anti-CD20 antibodies concentration without the addition of the mutant proteins (FIG. 1).

In other words, supplementation with appropriately mutated C2 proteins and the factor B increases the cytotoxic activity of the anticancer antibodies working through the complement system and simultaneously replenishes the pool of the used complement system components needed to sustain the cytotoxic potential of the human serum.

Point mutations ensuring the insensitivity of the complement system's convertases to the endogenous inhibitors (the so-called gain-of-function mutations), such as CD55, CD46, CD35, factor H, and resulting in an increased activity of the convertases, have been known to the researchers of the autoimmune phenomena. Mutations of this type located in the factor B were defined as an etiological factor of diseases such as C3 glomerulopathy and an atypical haemolytic-uraemic syndrome and in the international literature were univocally associated with pathological phenomena.

The novelty of the proposed solution consists in the use of such potentially pathogenic proteins as an immunotherapy supplement significantly increasing the cytotoxic activity of the immunotherapeutics.

Inhibition of the convertases is one of the main refractory mechanisms of the cancer cells to the complement-based therapies. Studies on model prevention of cancer resistance mechanisms include silencing the complement inhibitor's expression by a siRNA constructs transfection, or the use of bispecific antibodies that recognize the cancer cells' antigen determinant and simultaneously block the complement inhibitor (e.g., CD55).

A disadvantage and a practical limitation of the first solution is the necessity of a precise delivery of siRNA constructs to the cancer cells due to the widespread expression of the complement inhibitors in the human body. The latter of the mentioned approaches is limited to simultaneous inhibition of only one complement inhibitor, determined by the specificity of the antibody, while the cancer cells are producing or capturing several types of inhibitors from the environment.

Gain-of-function mutants ensure insensitivity of the complement convertases to more than one inhibitor type, and additionally, a creation of a multiple mutant which groups phenotypic characteristic of several single gain-of-function mutants is possible, which has been proven in the in vitro studies. The activity of a multiple mutant exceeds the cytotoxicity-enhancing activity of immunotherapeutics of single mutants. Moreover, a protein constructed that way is more versatile in relation to cancer cells displaying different patterns of complement inhibitor expression. A noticeable increase in the cytotoxic activity of the in vitro antibodies has been observed by supplementation of the factor B with multiple gain-of-function mutations, at a concentration corresponding to 25% physiological concentration of this protein in the serum (FIG. 2).

C2 is an element of the classical pathway, which is not activated spontaneously as in the alternative pathway (which consists of the factor B), but in response to the appearance of a specific stimulant, e.g., anticancer antibodies deposited onto the surface of the target cell. In other words, the process of the classical convertases formation with the participation of the mutated C2 protein may be controlled by coordinating its administration with the administration of immunotherapeutics. In contrast to the factor B, there's currently no known naturally occurring gain-of-function-type C2 mutation (or any other protein typical for the classical complement pathway) that has been identified as a cause of autoimmune disorders. Another benefit of the use of hyperactive C2 protein mutants is the C2's physiological concentration in the serum of only 25 μg/ml, which would require a significantly smaller amount of the recombinant C2 protein for effective supplementation than in the case of factor B supplementation (physiological concentration 180 μg/ml).

Considering that the naturally occurring gain-of-function-type mutants are unknown, but the C2 and the factor B proteins exhibit a significant degree of homology between them, C2 mutants have been created that correspond to the sequence of mutated, hyperactive factor B variants. Single and multiple gain-of-function C2 protein mutants showed an analogical to the mutated factor B, significant increase in the cytotoxic activity of the anti-CD20 antibodies (FIG. 3).

The creators of this invention postulate the supplementation with such mutants, with the use of the method of counteracting the cancer cells resistance to immunotherapeutics caused by the overexpression of complement inhibitors.

The mutants can be administered as a supplement, or in a pharmaceutically acceptable form, along with antibodies authorized for clinical use in anticancer therapy. In such pharmaceutical and therapeutic compositions, the mutants are beneficially used along with one, or more, pharmaceutically authorized carriers and optionally with other therapeutic components. The carriers have to be pharmaceutically authorized in the sense that they remain compatible with other components of the composition and are not excessively harmful to the recipient. The mutants are administered in amounts effective for achieving the desired pharmacological effect, as described above/in the examples. The compositions include those that are suitable for both parenteral and non-parenteral administration; specific ways of administration include also intravenous administration.

The objective of this invention is to provide the supplementation of accordingly mutated C2 proteins and/or factor B, which enhances the cytotoxic activity of the anticancer antibodies and could be used for standard anticancer therapy with antibodies.

The essence of the invention in question is point mutants of human proteins that make up the complement system's C3 and C5 convertases, where the individual mutations are:

For the factor B: —D279G, F286L, K323E, Y363A; D279G_F286L_K323E_Y363A—quadruple mutant;

For the C2 protein: —C261A, Q263G, Y347A, L348A; T442Q, double mutants C261A_Q263G and Y347A_Q263G, triple mutant Y347A_Q263G_T442Q.

Mutants which enhance the cytotoxic activity of the anticancer antibodies acting with the participation of the complement system.

A method of enhancing the anticancer antibodies' activity, which includes adding the mutants mentioned above.

A pharmaceutical composition, which includes the therapeutically effective amount of the mutants mentioned above.

The use of the abovementioned mutants to enhance the cytotoxic activity of the anticancer antibodies in the therapy.

The use of the abovementioned mutants to enhance the cytotoxic activity of the antibodies in the treatment of neoplastic diseases.

The use of the abovementioned mutants to enhance the cytotoxic activity of the serum in patients undergoing immunotherapy.

The terms used above, in the description and in the patent claims, have the following meaning:

Gain-of-function-type mutants—mutants in the proteins that build the alternative and classical convertases of the complement system, which result in increased activity of the convertases and/or their longer half-life.

Convertases—an enzyme complex formed during the complement cascade's activation, built from C3 protein and factor B fragments, C3bBb (alternative C3 convertase), C3bBbC3b (alternative C5 convertase) or C2, C4 and C3 protein fragments, respectively C4b2a (classical C3 convertase) and C4b2aC3b (classical CS convertase) respectively.

Supplementation—complementing the antibodies-based anticancer therapy (anticancer antibodies recognize the antigen determinants of the cancer cells).

The supporting factor/supplement is identical with supplementation.

Complement system—a group of proteins present in the blood serum, creating an enzymatic-proteolytic cascade resulting in the formation of a membrane-attacking complex. The description of the complement system and its individual proteins can be found in the literature such as "The Complement FactsBook," edited by Scott Barnum Theresa Schein, ed. 2, 2017, Academic Press.

FIGURES

Description of Figures

FIG. 1 demonstrates the cytotoxic effect of anti-CD20 antibodies, depending on the dose of antibodies.

FIG. 2 shows the cytotoxic effect of anti-CD20 antibodies after serum supplementation with recombinant gain-of-factor B factor mutations. The NHS (normal human serum) symbol was used for the serum without the addition of factor B, the WT (wild-type) symbol for the result of wild-type (non-mutated) supplementation and to the height of this bar (dashed line) reference to the calculations of statistically significant differences were made. Factor B mutants markings refer to the position of a given amino acid in the native protein (the numbering includes the signal sequence) and changes of a specific amino acid naturally occurring in a given position (letter before the amino acid position number expressed with the so-called one-letter code) to the amino acid resulting from the mutation (letter after position number expressed using the so-called single-letter code). The 4× marking corresponds to a quadruple mutant grouping the mutations D279G, F286L, K323E and Y363A. The ANOVA test with Dunnett post-test showed statistical significance for supplementation with the factor B quadruple gain-of-function mutation in the case of Raji cells at the significance level of p<0.05 (*).

FIG. 3A shows the anti-CD20 antibodies' cytotoxic effect after the serum supplementation (at the concentration optimal for visualizing the antibodies' cytotoxic effect in a given cell line—10% for the Raji cells and 20% for Namalwa cells, respectively) with C2 protein's gain-of-function recombinant mutants. Markings on the graph analogically to FIG. 2. The statistical significance according to the ANOVA test with Dunnett post-test at a level of p<0.001 is marked on the chart with a *** symbol and the significance at a level of p<0.05 with a * symbol.

FIG. 3B shows overall experiment results comprising two lower, suboptimal serum concentrations for which the cytotoxic effect of the anti-CD20 antibodies in a given cell line was tested.

FIG. 4 shows results of an additional experiment that compared the effect of single mutants ((Y347A, Q263G, T442Q), double mutant (Q263G_Y347A) and a triple mutant (Q263G_Y347A_T442Q)) on the Namalwa cells in an optimal serum concentration (20%, FIG. 4A) and additionally with two suboptimal serum concentrations (FIG. 4B). The markings on the charts accordingly to FIG. 2 and FIG. 3. The statistical significance according to the ANOVA test with a Dunnett post-test at a level of p<0.001 is marked on the chart with a * symbol, and the significance at a level of p<0.05 with a  symbol.

FIG. 5 shows results of an experiment in which the effect of C2 protein supplementation of the serum taken from patients treated with rituximab anti-CD20 antibody combined with an additional amount of another anti-CD20 antibody ofatumumab was tested. The effect of supplementation with the use of the recombined wild-type C2 protein (WT) and supplementation of the C2 protein multiple mutant (Q263G_Y347A_T442Q) were compared. The experiment was carried out with a 50% patient serum concentration (which reflected the physiological conditions) on the Namalwa cell line characterized by a low level of sensitivity to anti-CD20 antibodies. The ANOVA test with a Dunnett post-test showed a statistical significance to the multiple C2 protein gain-of-function mutant's supplementation in relation to a supplementation with unmutated (WT) protein at a significance level of p<0.01 (**).

FIG. 6 shows results of an experiment in which the 50% serum taken from patients after the rituximab administration (and thus containing some amount of rituximab unused by the immune system) was supplemented with a C2 protein multiple mutant (Q263G_Y347A_T442Q) or an unmutated protein (WT) and then was used in a cytotoxic test on Raji cells. The ANOVA test with a Dunnett post-test showed a statistical significance for supplementation with the multiple C2 protein gain-of-function mutant (causing a complete lysis of the Raji cells by the patients' sera) in relation to the supplementation of unmutated protein (WT) at a significance level of p<0.001 (***).

FIG. 7 shows Seq.1, which means a factor B's sequence with a signal sequence (single-letter amino acid code).

FIG. 8 shows Seq.2, which means a C2 protein's sequence with a signal sequence (single-letter amino acid code). The invention is illustrated by, but not limited to, the following examples:

EXAMPLE 1

Description of Methodology

Figure 1:
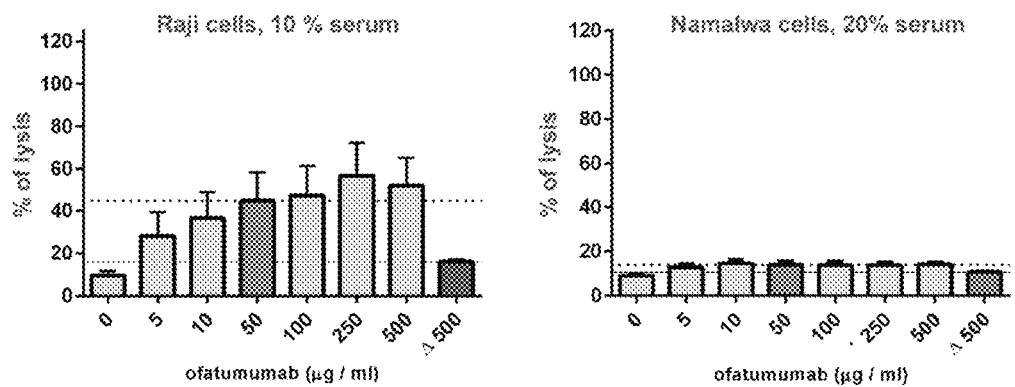

The cDNA reference sequences of the C2 proteins (accession number NM_000063.5) and the factor B (accession number NM_001710), additionally containing at the end 3' triplets for six histidine residues, have been optimized in terms of the GC pairs content, the presence of unfavorable secondary structures and the so-called rare codons through the ThermoFisher Scientific algorithm. The optimized sequences were then synthesized de novo and cloned to the pCEP4 expression plasmid. The constructs were once again verified with the help of the DNA sequencing. Plasmids verified for the sequence correctness were transformed into the DH5α strain $E.\ coli$ bacteria, from which the plasmid DNA was purified with the help of MidiPrep Kit (Qiagen) in the amount necessary for the eukaryotic cells' transfection. With the help of 30 µg of plasmid DNA and the Freestyle Max (ThermoFisher) reagent, a transfection of the HEK 293 Freestyle cells was performed. The cells were grown for seven days in the Freestyle 293 Expression Medium (ThermoFisher), while the growth medium was harvested on the second, fourth and seventh day after the transfection and resupplied with a fresh medium. The harvested, cell-conditioned medium was stored at −80 C until the protein purification process with the use of affinity chromatography. For this purpose, HisTrap FF crude (GE Healthcare) columns were used. Washing and balancing the columns were performed in a 20 mM Tris-HCl pH 8.0 buffer with addition of 1 mM of imidazole. The elution was conducted with the use of 0.7 M imidazole in the same buffer. The protein containing eluate fractions were merged, dialyzed on the PBS buffer and concentrated with the use of Vivaspin mwco. 10 kDa (Millipore) concentrator. On the basis of the cDNA optimized matrix, the cDNAs of factor B's single mutants D279G, F286L, K323E, and Y363A were created and the multiple mutant containing all of the substitutes mentioned above (4X), whereby the protein expression of a single F286L mutant was not achieved. Similarly, complement C2 protein single mutants (R243C, C261A, Q263G, S307E, Y347A, L348A, and T442Q) were created successively, as well as double mutants C261A_Q263G and Y347A_Q263G and the triple mutant Y347A_Q263G_T442Q.

The human Raji and Namalwa lymphoma cells expressing the CD20 marker on their surface were used for experiments. The Raji cells incubated in the presence of human serum are characterized by an average sensitivity to anti-CD20 antibodies, the maximum achievable level of cells' lysis oscillates within 50%. The Namalwa cells are characterized by a low sensitivity to the anti-CD20 antibodies due to the less favorable ratio of the CD20 molecules to the amount of the complement system's surface inhibitors, such as CD46, CD55 and CD59. Depending on the experiment, the Namalwa cells' lysis level in the presence of the serum and the anti-CD20 antibodies oscillated between 10% and 20%. The impact of the recombined factor B and the complement system's C2 protein on the anticancer activity of the anti-CD20 antibodies was tested in an in vitro cytotoxic test. Cells suspended in the RPMI medium with a 10% bovine serum addition were incubated with a 1 mM calcein derivative (calcein-AM), which is actively collected by living cells and metabolized to a fluorescent derivative. The incubation was carried out at 37° C. in a 5% CO2 environment for 30 minutes. The cells were then washed three times with a PBS buffer, suspended in a PBS buffer supplemented with a 1 mM $CaCl_2$ and $MgCl_2$ and added in the amount of 100.000 to the well of a V-shaped multiwell plate. After centrifugation and supernatant's removal, the cell pellet was suspended in human serum with anti-CD20 antibody (ofatumumab) in a standard concentration of 50

μg/ml. For the Raji cells, a 10% serum was used as a concentration for optimal visualization of the anti-CD20 antibodies' cytotoxic effect, for the Namalwa cells analogically the concentration was increased to 20%. Additionally, in selected experiments, a 50% serum collected from patients suffering from B cell-derived tumors treated with rituximab therapeutic anticancer antibody was used. The final reaction volume was 50 μl. The cells were incubated with the serum and with anti-CD20 antibodies for 30 minutes in a thermomixer (Eppendorf) at 37° C. and with shaking at 650 rpm. After the incubation was finished, another 50 μl of the PBS buffer was added and then the plate with the cells was centrifuged at a speed of 1000×G for two minutes. Eighty μl of the supernatant was moved to the wells of a 96-well flat-bottomed plate and the fluorescence of the collected supernatants was measured at excitation/emission wavelengths of 485 and 515 nm, respectively. The intensity of the fluorescence was directly proportional to the fluorescence of the derivative released from the cells due to the lysis induced by the complement system contained in the serum. The cells incubated with the heat-inactivated serum (56° C., 30 min) and thus lacking the complement's activity were treated as a negative control, i.e., a lysis independent of the complement system's activity.

In the first experiment it was shown that the increase in the dose of the anti-CD20 antibodies at a constant serum concentration does not significantly increase the percentage of the cells destroyed. (FIG. 1)

The bar marked with a Δ 500 symbol illustrated the effect of the maximum antibody concentration (500 μg/ml) and a heat-inactivated serum. Its height illustrates the level of lysis of cancer cells independent from the complement system. The ANOVA test with a Dunnett post-test did not show statistically significant differences between the 50 μg/ml concentration and the higher concentrations.

Figure 2:
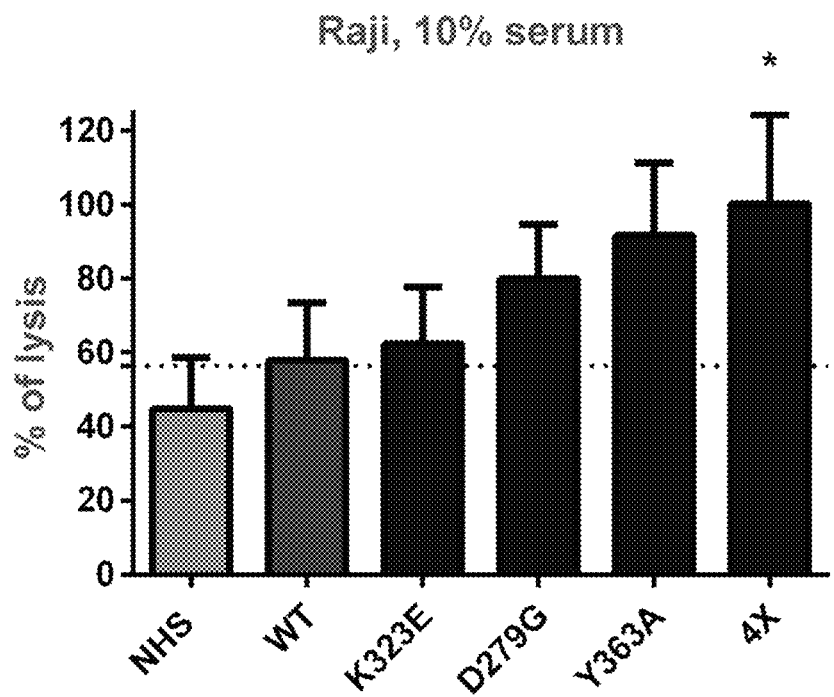
Figure 3:
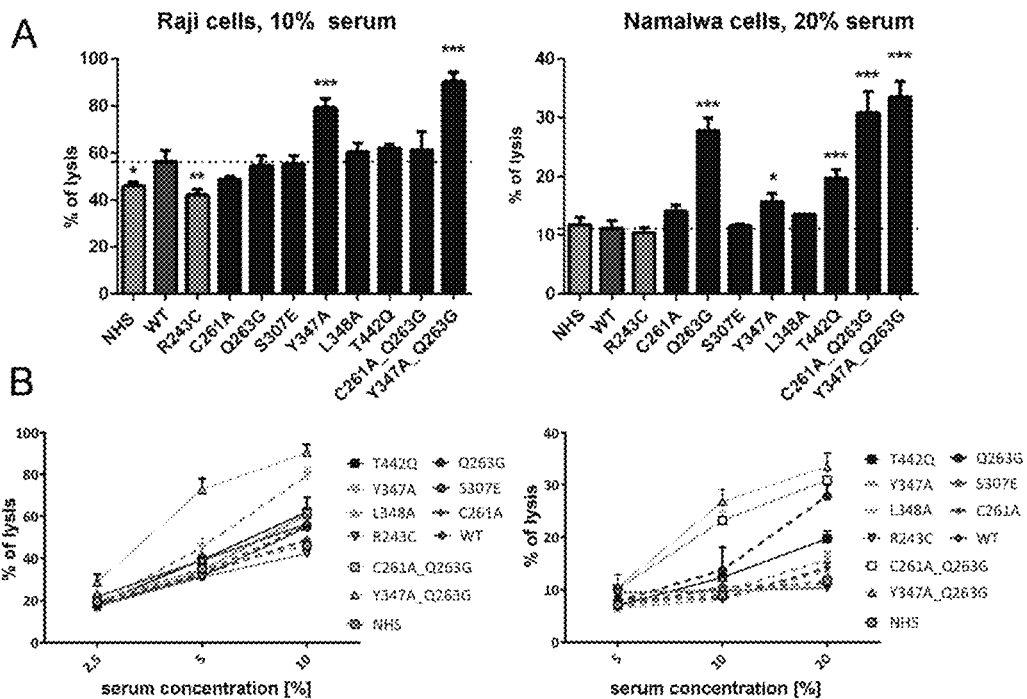

In contrast to increasing the antibodies' concentration, increasing the cytotoxic effect was possible after the serum (NHS) supplementation with factor B gain-of-function-type mutants (FIG. 2) and analogical complement's C2 protein mutants (FIG. 3). The concentration of the used mutants was equal to the physiological concentration of the proteins in the serum at a given concentration. For a 10% serum they were 2.5 μg/ml C2 and 20 μg/ml factor B and 5 μg/ml C2 protein for a 20% serum.

In the case of C2 protein, a panel of single gain-of-function mutants, two double mutants and one triple mutant, were made. The best effects (statistically significant increase in the cell's lysis percentage) in experiments performed in the Raji cells with single and double mutants were obtained for a Y347A_Q263G mutant—ANOVA test with a Dunnett post-test showed significance at a level of p<0.001 in the Raji cells case. A single Y347A mutant was at a similar level. It should be noted, however, that a noticeable effect of the Y347A_Q263G double mutant increasing the cytotoxicity of the anti-CD20 antibodies was already present at a suboptimal 5% serum concentration (FIG. 3B). In the case of Namalwa cells, statistically significant differences in the wild-type C2 protein supplementation were found in Q263G, T442Q, Y347A, C261A_Q263G, Y347A_Q263G and Y347A_Q263G_T442Q mutants (separate experiment depicted in FIG. 4). The R243C mutant was treated as a negative control due to the mutation's characteristic disrupting the structure, and hence, the function of the C2 protein. Double mutants, whose efficacy on the Namalwa line was demonstrated at a 20% serum's concentration, noticeably increased the cytotoxic effect also in a suboptimal 10% serum's concentration (FIG. 3B). The obtained results suggest that the multiple mutants work more efficiently under conditions of other complement proteins' deficiency, which can reflect an in vivo situation, in which the complement's pool is depleted due to earlier immunotherapy rounds or a primary or secondary immunodeficiency.

Figure 4:
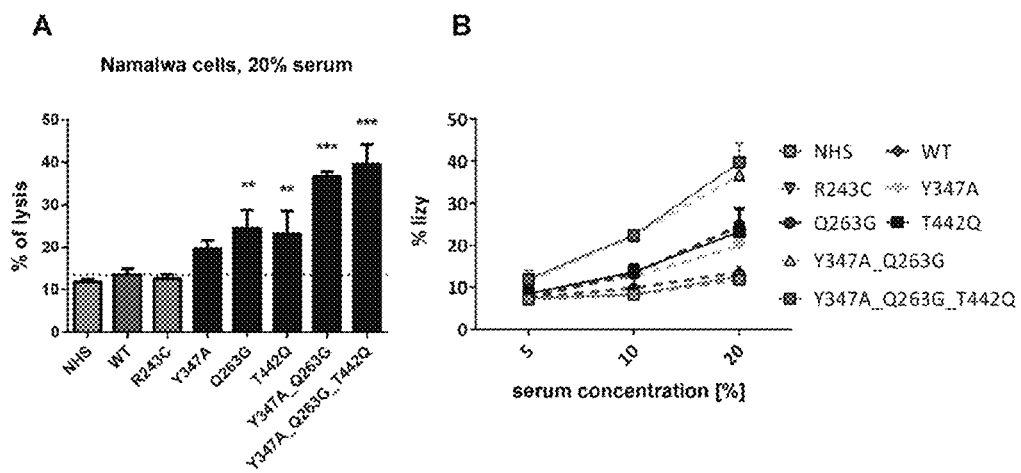

In a separate experiment on Namalwa cells the anti-CD20 antibodies' cytotoxic effect with supplementation with single (Y347A, Q263G, T442Q), double (Q263G_Y347A) and triple (Q263G_Y347A_T442Q) C2 protein mutants was compared (FIG. 4). The aim of the experiment was to show that the accumulation of single C2 protein gain-of-function-type mutations in one protein construct does not lead to the loss of C2 protein activity but may cause an additive effect manifested by both a higher antibodies' cytotoxicity at an optimal serum concentration and a significantly higher percentage of killed cells at a suboptimal serum concentration, in comparison to the results obtained under analogical conditions for single mutants. Such actions are desirable from a practical point of view because it ensures a much more beneficial supplementation effect.

Figure 5:
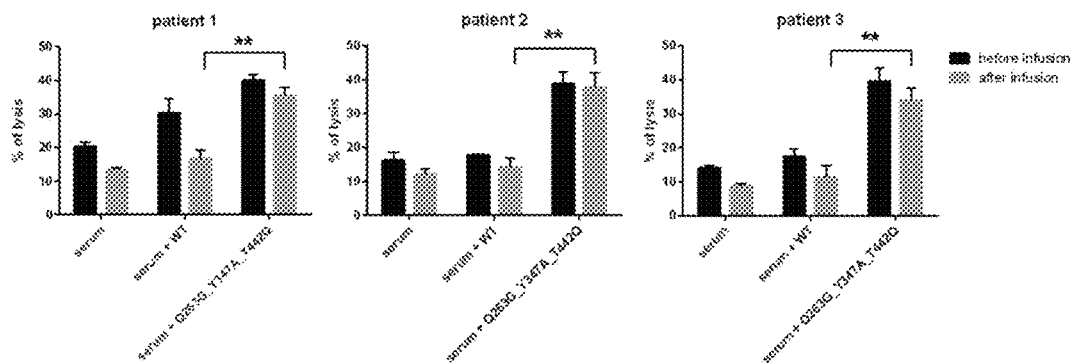

In the next experiment, the Namalwa line cells along with sera (in the final 50% concentration corresponding to the physiological conditions) taken from the patients with B cell-derived tumors treated with rituximab were used. Serum samples were taken from patients directly before and directly after the administration of rituximab. The rituximab's administration causes a mass activation of the complement system in this type of patients, which in turn is manifested by a decreased serum's cytotoxic activity after the drug administration, due to the consumption of the complement protein pool. A sustained state of decreased cytotoxic activity may cause a decreased rituximab's efficacy in relation to cancer cells that have not been killed during the first administration of the drug. The sera were first supplemented with another anti-CD20 antibody, analogical to rituximab: ofatumumab. Next, the sera were supplemented with a recombinant wild-type C2 protein and Q263G_Y347A_T442Q multiple C2 protein mutant at a concentration of 12.5 μg/ml. The cytotoxic test results showed that supplementing the patients' sera with a multiple mutant can not only increase the cytotoxic effect of the patient before the drug administration but can also counteract the reduction of the cytotoxic activity of patients' sera following the rituximab's administration at the time when the drug's activity is leading to exhaustion of the complement system's protein pool (FIG. 5). The described multiple mutant's effect could not be obtained by a supplementation with a recombinant, wild-type (WT) C2 protein variant.

Figure 6:
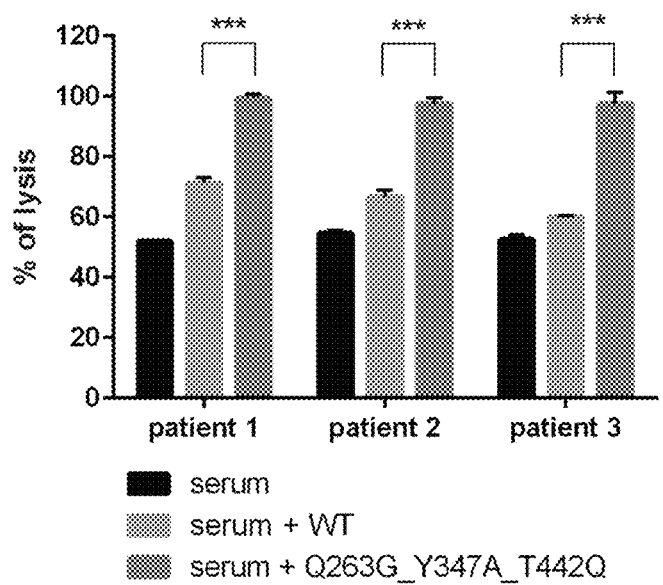

An analogical experiment, in which the effects of the wild-type (WT) and triple-mutated (Q263G_Y347A_T442Q) C2 protein supplementation on the cytotoxic potential of the sera collected from the same patients as in FIG. 5, although without the addition of saturating concentration of ofatumumab, was carried out on the Raji cell line (FIG. 6). In this experimental setup, the only present anticancer drug was the excess rituximab remaining after the intravenous administration, which was not used by the immune system to the cancer cell elimination. The addition of 12.5 μg/ml of a triple-mutated C2 protein allowed for a complete lysis of the Raji cells by sera collected from patients after the rituximab's infusion, whereas the result for the sera without the C2 addition or with an addition of an unmutated (WT) C2 protein ranged between 50% and 70% of a complete lysis depending on the patient. The obtained results illustrate the example, when not the bioavailability of the drug, but the decrease in the serum's cytotoxic activity is the factor limiting a successful anticancer antibody therapy and when the of gain-of-function C2 protein mutants can significantly increase the effectiveness of the drug already present in the patient's bloodstream by strengthening the complement system's activity.

Results Summary:

It has been shown that some gain-of-function-type mutations in the C2 proteins and in the factor B can significantly increase the cytotoxic activity of the anti-CD20 antibodies such as ofatumumab, for example. An analogical supplementation effect is to be expected for other anticancer antibodies known from literature (e.g., rituximab, alemtuzumab) acting via the complement system. It has been shown, however, that a similar effect cannot be reproduced by increasing the dose of antibodies alone. An accumulation of many point mutations in one protein may give a cumulative effect, as in the case of a quadruple factor B D279G_F286L_K323E_Y363A mutant or the C2 protein Y347A_Q263G, C261A_Q263G, Y347A_Q263G_T442Q mutants. The use of multiple C2 protein mutants such as Q263G_Y347A_T442Q was able to counteract the decrease in the cytotoxic potential of the sera collected from the patients after the anti-CD20 antibodies administration and also to significantly better utilize the anticancer potential of the antibodies remaining in the patients' sera after the drug administration. As an element of novelty, we emphasize the use of such mutants as a universal supplement in antibodies anticancer immunotherapy.

LITERATURE

1. Stasilojc G, Osterborg A, Blom A M, Okroj M. New perspectives on complement mediated immunotherapy. Cancer Treat Rev 2016; 45:68-75.
2. Urban A, Borowska A, Felberg A, van den Heuvel L, Stasilojc G, Volokhina, et al. Gain of function mutant of complement factor B K323E mimics pathogenic C3NeF autoantibodies in convertase assays. Autoimmunity 2018; 51:18-24.
3. Fishelson Z, Donin N, Zell S, Schultz S, Kirschfink M. Obstacles to cancer immunotherapy: expression of membrane complement regulatory proteins (mCRPs) in tumors. Mol Immunol 2003; 40:109-23.
4. Mamidi S, Hone S, Teufel C, Sellner L, Zenz T, Kirschfink M. Neutralization of membrane complement regulators improves complement-dependent effector functions of therapeutic anticancer antibodies targeting leukemic cells. Oncoimmunology 2015; 4:e979688.
5. Macor P, Secco E, Mezzaroba N, Zorzet S, Durigutto P, Gaiotto T, et al. Bispecific antibodies targeting tumor-associated antigens and neutralizing complement regulators increase the efficacy of antibody-based immunotherapy in mice. Leukemia 2015; 29:406-14.
6. Okroj M, Eriksson I, Osterborg A, Blom A M. Killing of CLL and NHL cells by rituximab and ofatumumab under limited availability of complement. Med Oncol 2013; 30:759.

The invention claimed is:

1. A composition comprising a mutant Factor B protein, wherein the mutant Factor B protein is a Factor B protein with D279G, F286L, K323E, and Y363A mutations, wherein the mutations are relative to the Factor B protein of SEQ ID NO.:1 and
wherein the composition enhances the cytotoxic activity of one or more immunotherapeutics.

2. A composition comprising a mutant C2 protein, wherein the mutant C2 protein is selected from the group consisting of:
a C2 protein with C261A and Q263G mutations;
a C2 protein with Q263G and Y347A mutations; and
a C2 protein with Y347A, Q263G, and T442Q mutations, wherein the mutations are relative to the C2 protein of SEQ ID NO.:2, and
wherein the composition enhances the cytotoxic activity of one or more immunotherapeutics.

3. A pharmaceutical composition comprising:
a therapeutically effective amount of a composition of claim 1; and
one or more anti-cancer antibodies.

4. The pharmaceutical composition of claim 3, wherein one or more anti-cancer antibodies are anti-CD20 antibodies.

5. A method of treating a patient having a neoplastic disease comprising:
administering a therapeutically effective amount of a composition of claim 1 to a patient in need thereof in combination with one or more immunotherapeutics.

6. The method of claim 5, wherein one or more immunotherapeutics are anti-CD20 antibodies.

7. The method of claim 6, wherein the neoplastic disease is cancer.

8. A pharmaceutical composition comprising:
a therapeutically effective amount of a composition of claim 2; and
one or more anti-cancer antibodies.

9. The pharmaceutical composition of claim 8, wherein one or more anti-cancer antibodies are anti-CD20 antibodies.

10. A method of treating a patient having a neoplastic disease comprising:
administering a therapeutically effective amount of a composition of claim 2 to a patient in need thereof in combination with one or more immunotherapeutics.

11. The method of claim 10, wherein one or more immunotherapeutics are anti-CD20 antibodies.

12. The method of claim 11, wherein the neoplastic disease is cancer.

* * * * *